(12) United States Patent
Parvin et al.

(10) Patent No.: US 11,402,327 B2
(45) Date of Patent: Aug. 2, 2022

(54) OPTICAL IMAGING BASED ON SPECTRAL SHIFT ASSESSMENT

(71) Applicants: Parviz Parvin, Tehran (IR); Amir Jafargholi, Tehran (IR); Ali Bavali, Tehran (IR); Mohammad Amin Bassam, Tehran (IR); Parisa Zhalefar, Tehran (IR); Azadeh Niazi, Tehran (IR); Seyed Ali Dehghanian, Tehran (IR); Zahra Khodabakshi, Tehran (IR)

(72) Inventors: Parviz Parvin, Tehran (IR); Amir Jafargholi, Tehran (IR); Ali Bavali, Tehran (IR); Mohammad Amin Bassam, Tehran (IR); Parisa Zhalefar, Tehran (IR); Azadeh Niazi, Tehran (IR); Seyed Ali Dehghanian, Tehran (IR); Zahra Khodabakshi, Tehran (IR)

( * ) Notice: Subject to any disclaimer, the term of this patent is extended or adjusted under 35 U.S.C. 154(b) by 366 days.

(21) Appl. No.: 16/706,748

(22) Filed: Dec. 8, 2019

(65) Prior Publication Data

US 2020/0110031 A1 Apr. 9, 2020

Related U.S. Application Data

(60) Provisional application No. 62/777,074, filed on Dec. 8, 2018.

(51) Int. Cl.
*G01N 21/64* (2006.01)
*G02B 21/16* (2006.01)
*G02B 21/36* (2006.01)

(52) U.S. Cl.
CPC ..... *G01N 21/6402* (2013.01); *G01N 21/6458* (2013.01); *G02B 21/16* (2013.01);
(Continued)

(58) Field of Classification Search
CPC .... G02B 21/367; G02B 21/365; G02B 21/16; G01N 2021/6463; G01N 2021/6484;
(Continued)

(56) References Cited

U.S. PATENT DOCUMENTS 9,655,523 B2 * 5/2017 Hillman ............... A61B 5/0073
2020/0110031 A1 * 4/2020 Parvin ............... G01N 21/6402
(Continued)

*Primary Examiner* — John R Lee
(74) *Attorney, Agent, or Firm* — Bajwa IP Law Firm; Haris Zaheer Bajwa

(57) ABSTRACT

A method for optical imaging based on spectral shift assessment. The method includes generating a sample by mixing an object with a fluorophore, stimulating the sample by emitting a laser beam, extracting a plurality of fluorescence spectra from a plurality of fluorescence emissions emitted from the sample, detecting a plurality of fluorescence peaks and a plurality of peak wavelengths in the plurality of fluorescence spectra, extracting a plurality of fluorophore concentrations from a database, and generating a concentration image. The plurality of peak wavelengths are detected by detecting a respective peak wavelength of the plurality of peak wavelengths. Each of the plurality of fluorophore concentrations is associated with a respective peak wavelength of the plurality of peak wavelengths. The concentration image includes a first plurality of pixels. The concentration image is generated based on a respective fluorophore concentration of the plurality of fluorophore concentrations.

20 Claims, 15 Drawing Sheets

(52) U.S. Cl.
CPC .. *G02B 21/365* (2013.01); *G01N 2201/06113* (2013.01); *G01N 2201/126* (2013.01)

(58) Field of Classification Search
CPC ..... G01N 2021/6406; G01N 2201/126; G01N 2201/06113; G01N 21/645; G01N 21/6456; G01N 21/6458; G01N 21/64; G01N 21/6404; G01N 21/6402
See application file for complete search history.

(56) References Cited

U.S. PATENT DOCUMENTS

2020/0142174 A1\* 5/2020 Duocastella ....... H04N 5/23212
2022/0047164 A1\* 2/2022 Dacosta .................. A61B 5/01

\* cited by examiner

OPTICAL IMAGING BASED ON SPECTRAL SHIFT ASSESSMENT

CROSS-REFERENCE TO RELATED APPLICATION

This application claims the benefit of priority from U.S. Provisional Patent Application Ser. No. 62/777,074, filed on Dec. 8, 2018, and entitled "OPTICAL IMAGING MICROSCOPY BASED ON THE SPECTRAL SHIFT-LASER INDUCED FLUORESCENCE SPECTROSCOPY," which is incorporated herein by reference in its entirety.

TECHNICAL FIELD

The present disclosure generally relates to optical imaging, and particularly, to fluorescence spectroscopy.

BACKGROUND

Laser-induced fluorescence (LIF) imaging is widely used in various fields such as medicine, photobiology, and material identification. In LIF imaging, objects of interest are mixed with fluorophores and then, molecules of fluorophores are stimulated by exposing them to a laser light. LIF imaging is based on spectroscopy of emitted light from fluorophores, which gives light intensity as a function of wavelength. Intensity of emitted light from each object segment depends on a concentration of fluorophore in that segment. Therefore, intensity of emitted light can be used to provide an image that gives distribution of fluorophore concentration over an object. Each material has its own fingerprint of concentration distribution. Hence, comparing an obtained image with these fingerprints may facilitate identification of an object of interest, for example, identification of healthy tissues from cancerous ones.

Intensity of emitted light, however, may be impacted by various phenomena such as dynamic suppression, resonance energy transfer, and scattering. Intensity may also be impacted by imaging setup, laser power, and may require precise calibration of imaging devices. Therefore, spectroscopy may be subjected to uncertain factors that may lead to images with inexact data. As a result, details of obtained images may be lost or altered which, for example, may limit discrimination of healthy and cancerous tissues in clinical applications. There is, therefore, a need for an optical imaging method and system that may provide robust images whose quality is not or minimally impacted by different variations in environment and system parameters.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for optical imaging based on spectral shift assessment. An exemplary method may include generating a sample by mixing an object with a fluorophore, stimulating the sample by emitting a laser beam, extracting a plurality of fluorescence spectra from a plurality of fluorescence emissions emitted from the sample, detecting a plurality of fluorescence peaks and a plurality of peak wavelengths in the plurality of fluorescence spectra, extracting a plurality of fluorophore concentrations from a database, and generating a concentration image. An exemplary sample may include a plurality of segments. An exemplary laser beam may include a laser wavelength and may be emitted on each of the plurality of segments. In an exemplary embodiment, each segment of the plurality of segments may include a respective mixture of the fluorophore and a biological material.

In an exemplary embodiment, the plurality of fluorescence spectra may be extracted utilizing a spectrometer by extracting each of the plurality of fluorescence spectra from a respective fluorescence emission of the plurality of fluorescence emissions. In an exemplary embodiment, the respective fluorescence emission may be emitted from a respective segment of the plurality of segments.

In an exemplary embodiment, the plurality of fluorescence peaks and the plurality of peak wavelengths may be detected utilizing one or more processors. In an exemplary embodiment, the plurality of fluorescence peaks may be detected by detecting a respective fluorescence peak of the plurality of fluorescence peaks in each of the plurality of fluorescence spectra. In an exemplary embodiment, the plurality of peak wavelengths may be detected by detecting a respective peak wavelength of the plurality of peak wavelengths in each of the plurality of fluorescence spectra. In an exemplary embodiment, the respective peak wavelength may be associated with the respective fluorescence peak.

In an exemplary embodiment, the plurality of fluorophore concentrations may be extracted utilizing the one or more processors. An exemplary database may be associated with the laser wavelength and may include variations of fluorescence intensity with wavelength for different concentrations of the fluorophore. In an exemplary embodiment, each of the plurality of fluorophore concentrations may be associated with a respective peak wavelength of the plurality of peak wavelengths. An exemplary concentration image may be generated utilizing the one or more processors and may include a first plurality of pixels. In an exemplary embodiment, the concentration image may be generated by assigning a respective intensity level to each of the first plurality of pixels based on a respective fluorophore concentration of the plurality of fluorophore concentrations. In an exemplary embodiment, the respective fluorophore concentration may be associated with a respective segment of the plurality of segments.

An exemplary method may further include generating a fluorescence image. An exemplary fluorescence image may include a second plurality of pixels. In an exemplary embodiment, the fluorescence image may be generated by assigning a respective intensity level to each of the second plurality of pixels based on a respective fluorescence peak associated with a respective segment of the plurality of segments.

In an exemplary embodiment, stimulating the sample by emitting the laser beam may include placing the sample under an objective lens of an optical microscope and focusing the laser beam on each of the plurality of segments. In an exemplary embodiment, the laser beam may be focused by passing the laser beam through a first eyepiece of the optical microscope. In an exemplary embodiment, focusing the laser beam may include positioning a focal point of the laser beam at a respective center of each of the plurality of segments. An exemplary focal point may be positioned by moving the respective center to a location of the focal point.

In an exemplary embodiment, the respective center may be moved utilizing a translation stage.

In an exemplary embodiment, extracting a plurality of fluorescence spectra may include capturing the respective fluorescence emission by an optical fiber and sending the respective fluorescence emission to the spectrometer via the optical fiber. In an exemplary embodiment, capturing the respective fluorescence emission may include capturing the respective fluorescence emission through an emission path. An exemplary emission path may include the objective lens and a second eyepiece of the optical microscope. In an exemplary embodiment, capturing the respective fluorescence emission may include positioning a main axis of a tip of the optical fiber in a direction of the laser beam.

In an exemplary embodiment, mixing the object with the fluorophore may include mixing each of the plurality of segments with the fluorophore. In an exemplary embodiment, each of the plurality of segments may include a biological material. In an exemplary embodiment, mixing the object with the fluorophore may include injecting a biocompatible fluorophore into a biological tissue. In an exemplary embodiment, mixing the biological tissue with the fluorophore may include mixing the biological tissue with one of Rhodamine 6G (RD6G), coumarin, or fluorescein.

Other exemplary systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an exemplary method and system for optical imaging based on spectral shift assessment. The exemplary method may provide images that show a distribution of concentration of a fluorophore over a sample of interest. To this end, a sample may be generated by mixing an object with a fluorophore. Then, the sample may be exposed to a laser beam with a specific laser wavelength. The laser beam may stimulate the fluorophore and the fluorophore may generate a fluorescence emission. Then, a fluorescence spectrum may be extracted from the fluorescence emission for each segment of the sample. The fluorescence spectrum of each segment may be processed and a peak fluorescence, i.e., a maximum amplitude in the fluorescence spectrum and a peak wavelength corresponding to the peak fluorescence may be detected. Comparing the peak wavelength and the laser wavelength may give a spectral shift for each segment of the sample. Referring to a database of the fluorophore, which may assign a unique concentration to a specific spectral shift, a concentration may be inferred from the given spectral shift for each segment of the sample. Finally, concentration image of the sample may be generated using concentrations of all sample segments.

Figure 1A:
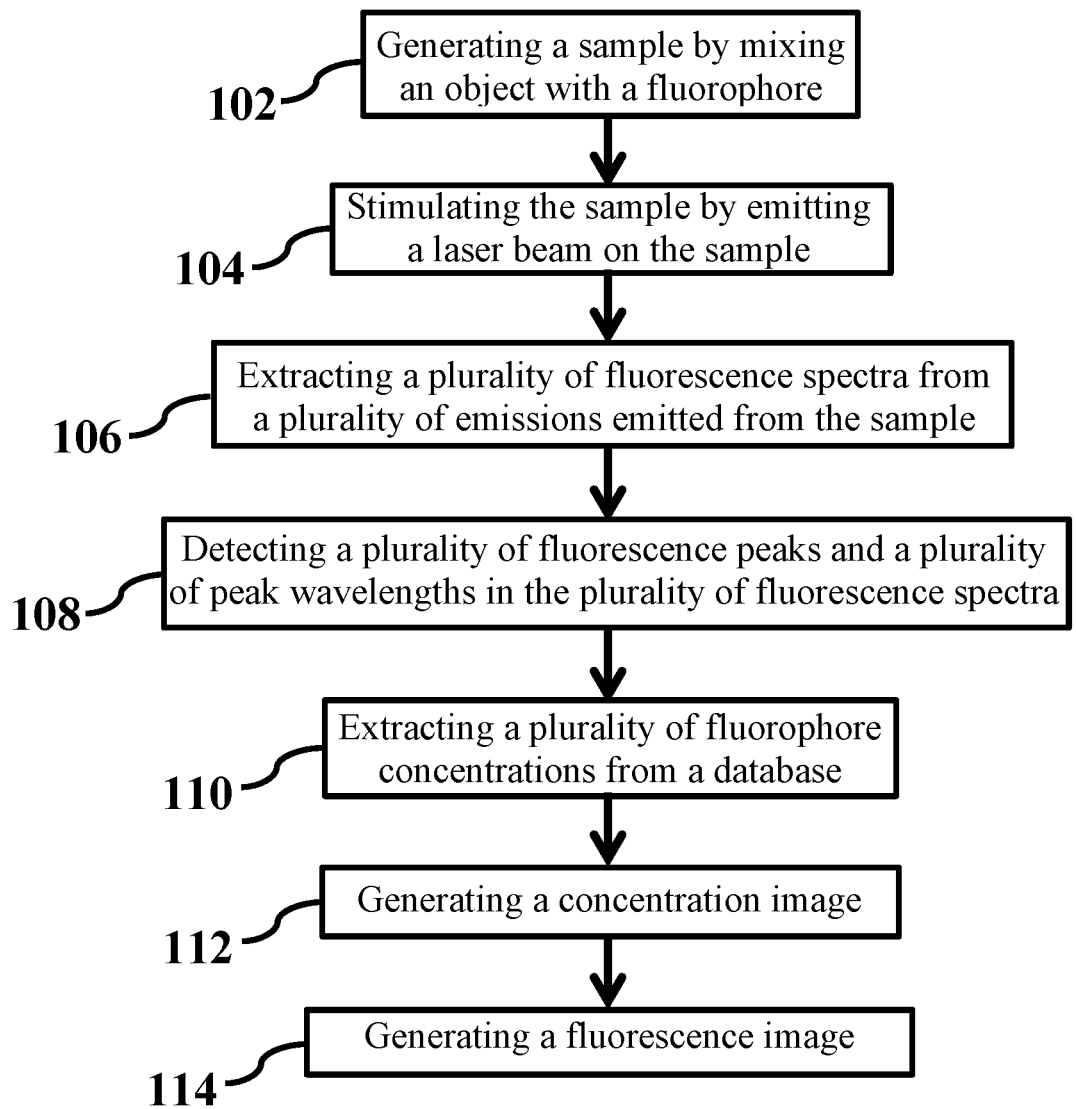
FIG. 1A shows a flowchart of a method for optical imaging based on spectral shift assessment, consistent with one or more exemplary embodiments of the present disclosure.

FIG. 1A shows a flowchart of a method for optical imaging based on spectral shift assessment, consistent with one or more exemplary embodiments of the present disclosure. An exemplary method 100 may include generating a sample by mixing an object with a fluorophore (step 102), stimulating the sample by emitting a laser beam on the sample (step 104), extracting a plurality of fluorescence spectra from a plurality of fluorescence emissions emitted from the sample (step 106), detecting a plurality of fluorescence peaks and a plurality of peak wavelengths in the plurality of fluorescence spectra (step 108), extracting a plurality of fluorophore concentrations from a database (step 110), generating a concentration image (step 112), and generating a fluorescence image (step 114). In an exemplary embodiment, the sample may include a plurality of segments. In an exemplary embodiment, the laser beam may include a laser wavelength and may be emitted on each of the plurality of segments. In an exemplary embodiment, each segment of the plurality of segments may include a respective mixture of the fluorophore and a biological material.

For further detail with respect to step 102, in an exemplary embodiment, mixing the object with the fluorophore may include mixing each of the plurality of segments with the fluorophore. In an exemplary embodiment, each of the plurality of segments may include a biological material. In an exemplary embodiment, method 100 may be utilized for both in vivo and in vitro imaging. In case of in vivo imaging, the sample may be generated by mixing a biological tissue and a biocompatible fluorophore via injecting the biocompatible fluorophore into the biological tissue. Examples of biomaterial fluorophores may include doxorubicin, irinotecan, gemcitabine, and navelbine. For in vitro imaging, an exemplary object of interest may be mixed with a non-biocompatible fluorophore. An exemplary non-biocompatible fluorophore may include one of Rhodamine 6G (RD6G), coumarin, or fluorescein.

Figure 2A:
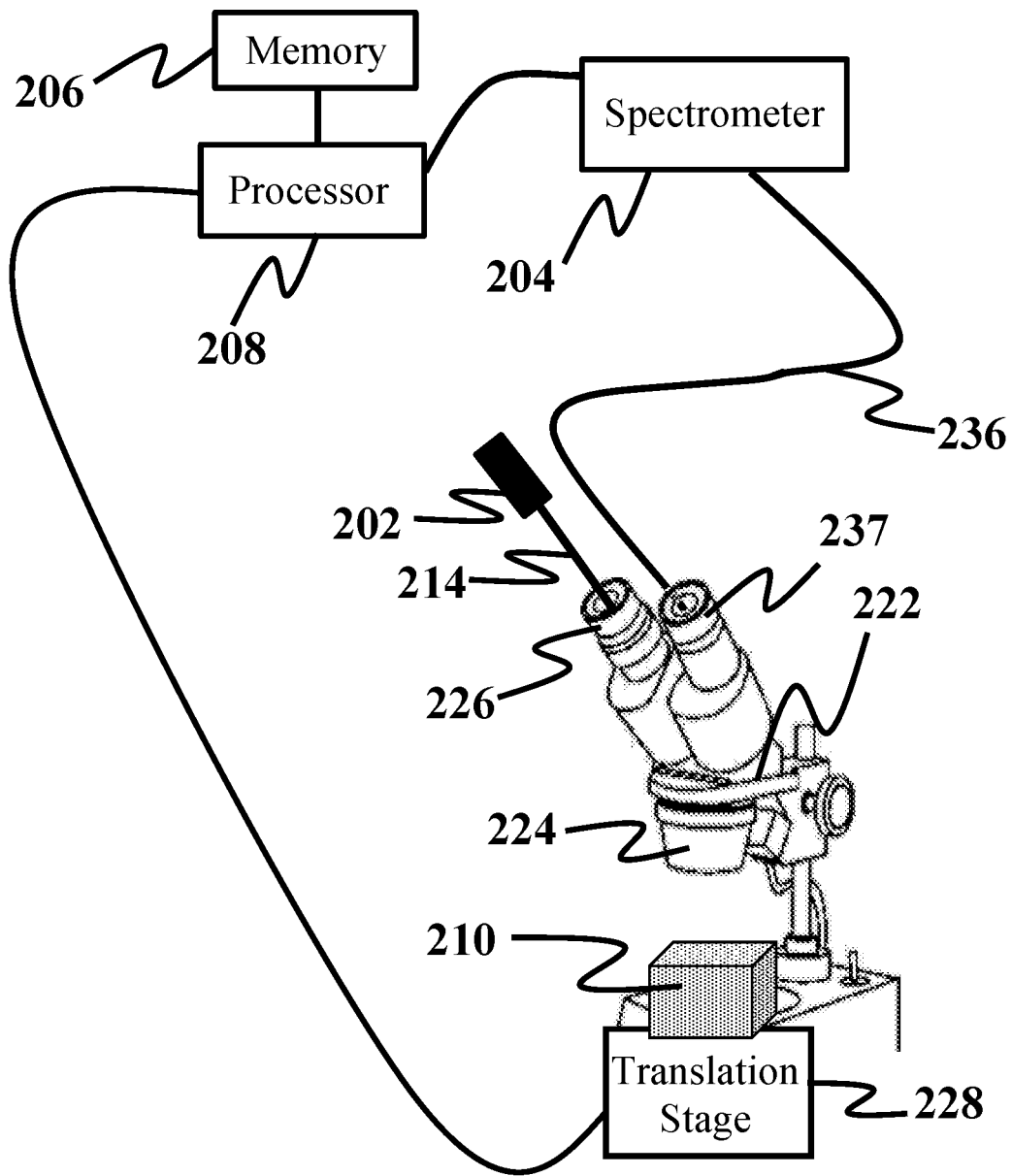
FIG. 2A shows a schematic of a system for optical imaging based on spectral shift assessment, consistent with one or more exemplary embodiments of the present disclosure.

FIG. 2A shows a schematic of a system for optical imaging based on spectral shift assessment, consistent with one or more exemplary embodiments of the present disclosure. In an exemplary embodiment, different steps of method 100 may be implemented utilizing an exemplary system 200. In an exemplary embodiment, system 200 may include a laser 202, a spectrometer 204, a memory 206, and a processor 208. In an exemplary embodiment, system 200 may further include an optical microscope 222. In an exemplary embodiment, optical microscope 222 may include an objective lens 224, a first eyepiece 226, and a second eyepiece 237. In an exemplary embodiment, system 200 may further include a translation stage 228. In an exemplary embodiment, system 200 may further include an optical fiber 236. Further detail with respect to each of the above mentioned elements is provided below.

Figure 1B:
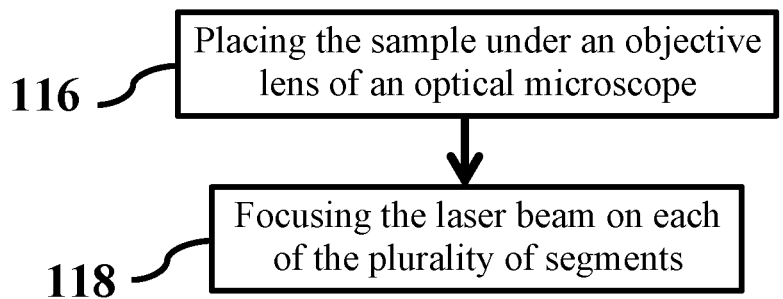
FIG. 1B shows a flowchart of stimulating a sample by emitting a laser beam on the sample, consistent with one or more exemplary embodiments of the present disclosure.
Figure 2B:
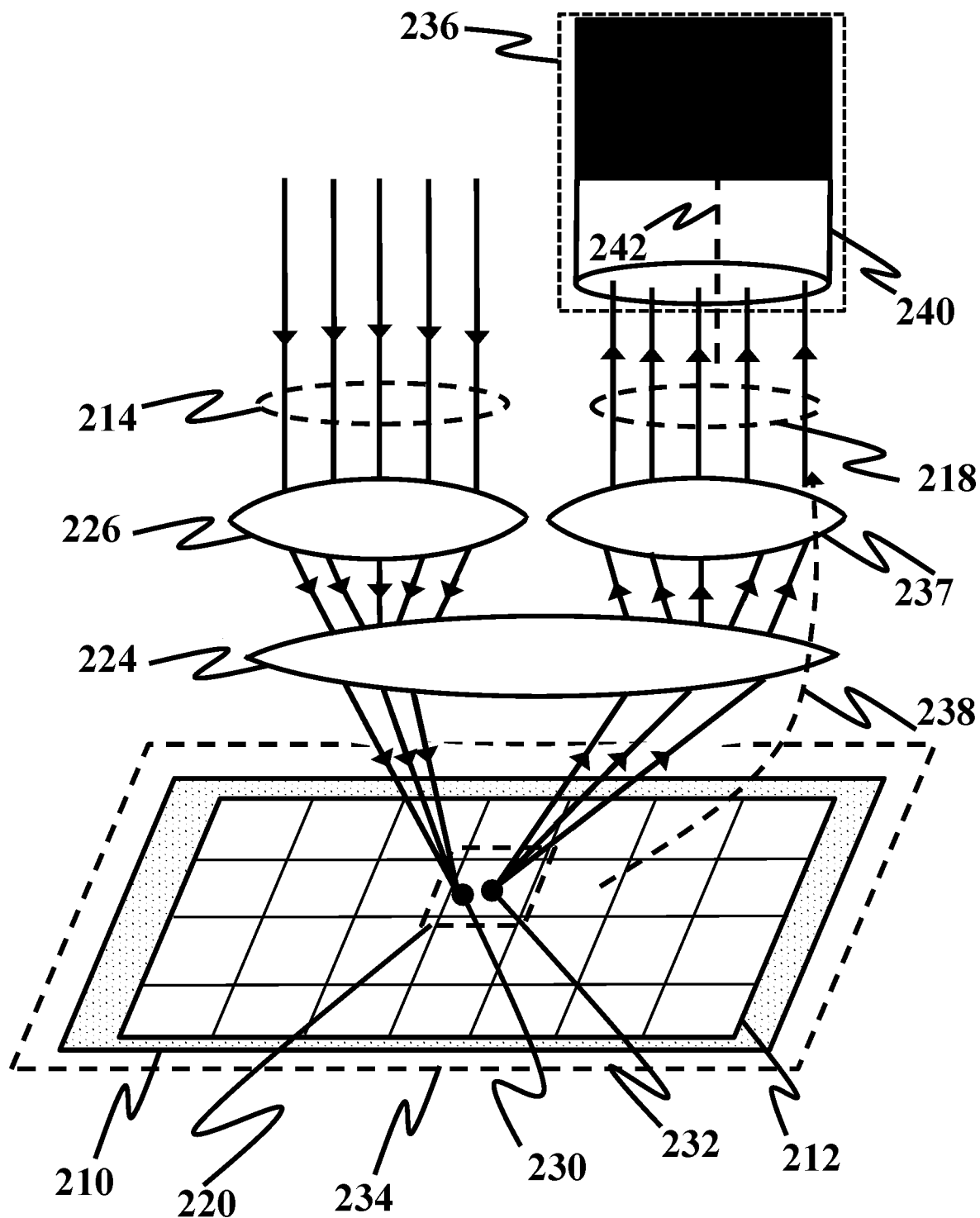
FIG. 2B shows a sample stimulated by a laser beam, consistent with one or more exemplary embodiments of the present disclosure.

FIG. 2B shows a sample stimulated by a laser beam, consistent with one or more exemplary embodiments of the present disclosure. In an exemplary embodiment, laser 202 may be configured to stimulate a sample 210, as explained below in further detail with respect to FIG. 1B. In an exemplary embodiment, sample 210 may include a plurality of segments 212. In an exemplary embodiment, each of plurality of segments 212 may include a respective mixture of a fluorophore and a biological material. In an exemplary embodiment, system 200 may further include a needle. An exemplary needle may be configured to aid in generating sample 210 by injecting a biocompatible fluorophore into the biological material.

For further detail with regards to step 104, in an exemplary embodiment, sample 210 may be stimulated by emitting a laser beam 214 on each of plurality of segments 212. In an exemplary embodiment, laser beam 214 may include a laser wavelength and the fluorophore may include an absorption band. An exemplary absorption band may include a set of absorption lines in which the fluorophore may absorb the laser beam. Therefore, in order for the fluorophore to emit a fluorescence emission, an exemplary laser wavelength may belong to the absorption band of the fluorophore.

FIG. 1B shows a flowchart of stimulating a sample by emitting a laser beam on the sample, consistent with one or more exemplary embodiments of the present disclosure. In an exemplary embodiment, stimulating the sample by emitting the laser beam on the sample (step 104) may include placing the sample under an objective lens of an optical microscope (step 116) and focusing the laser beam on each of the plurality of segments (step 118).

For further detail regarding step 116, in an exemplary embodiment, objective lens 224 may be configured to be placed above sample 210. For further detail regarding step 118, in an exemplary embodiment, first eyepiece 226 may be configured to focus laser beam 214 on each of plurality of segments 212. In an exemplary embodiment, translation stage 228 may be configured to position a focal point 230 of laser beam 214 at a respective center 232 of each of plurality of segments 212 by moving sample 210 with a predefined step size. In an exemplary embodiment, the predefined step size of translation stage 228 may determine a precision of positioning focal point 230. In an exemplary embodiment, focal point 230 may be positioned by moving respective center 232 to a location of focal point 230.

Figure 3:
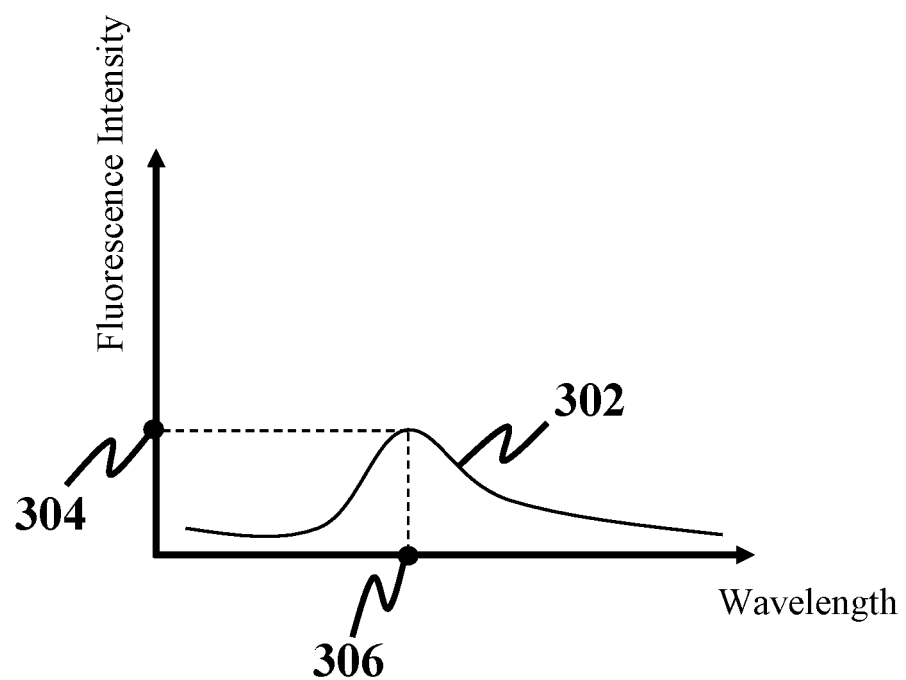
FIG. 3 shows a fluorescence spectrum, consistent with one or more exemplary embodiments of the present disclosure.

In further detail with respect to step 106, FIG. 3 shows a fluorescence spectrum, consistent with one or more exemplary embodiments of the present disclosure. Referring to FIGS. 2A-3, in an exemplary embodiment, spectrometer 204 may be configured to extract a plurality of fluorescence spectra (each similar to a fluorescence spectrum 302) from a plurality of fluorescence emissions. In an exemplary embodiment, the plurality of fluorescence emissions may be emitted from sample 210. In an exemplary embodiment, the plurality of fluorescence spectra may be extracted by extracting each of the plurality of fluorescence spectra from a respective fluorescence emission 218 of the plurality of fluorescence emissions, as described in further detail with respect to FIG. 1C. In an exemplary embodiment, respective fluorescence emission 218 may be emitted from a respective segment 220 of plurality of segments 212.

Figure 1C:
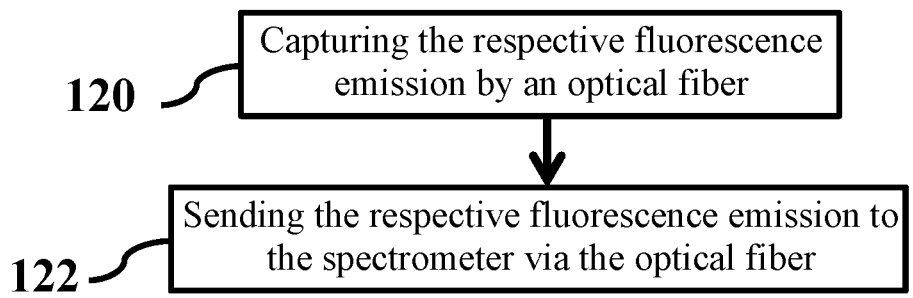
FIG. 1C shows a flowchart of extracting a plurality of fluorescence spectra, consistent with one or more exemplary embodiments of the present disclosure.

FIG. 1C shows a flowchart of extracting a plurality of fluorescence spectra, consistent with one or more exemplary embodiments of the present disclosure. In an exemplary embodiment, extracting a plurality of fluorescence spectra may include capturing the respective fluorescence emission by an optical fiber (step 120) and sending the respective fluorescence emission to the spectrometer via the optical fiber (step 122).

In further detail with respect to step 120, in an exemplary embodiment, optical fiber 236 may be configured to capture respective fluorescence emission 218. In an exemplary embodiment, optical fiber 236 may also be configured to send respective fluorescence emission 218 to spectrometer 204. In an exemplary embodiment, second eyepiece 237 may be configured to receive respective fluorescence emission 218 through objective lens 224. In an exemplary embodiment, second eyepiece 237 may also be configured to send respective fluorescence emission 218 to optical fiber 236. In an exemplary embodiment, capturing respective fluorescence emission 218 may include capturing respective fluorescence emission 218 through an emission path 238. In an exemplary embodiment, emission path 238 may include objective lens 224 and second eyepiece 237.

In an exemplary embodiment, optical fiber 236 may include a tip 240. In an exemplary embodiment tip 240 may have a main axis 242. In an exemplary embodiment, main axis 242 may be in the direction of laser beam 214.

Referring again to FIGS. 2B and 3, in an exemplary embodiment, a field of view of second eyepiece 237 may be referred to as a region on sample 210 from which fluorescence emissions may be captured. In an exemplary embodiment, a field of view of second eyepiece 237 may be larger than respective segment 220. In this case, second eyepiece 237 may receive a plurality of fluorescence emissions from adjacent segments of respective segment 220. As a result, each of the plurality of fluorescence spectra may be interfered by a plurality of fluorescence spectra associated with fluorescence emissions from adjacent segments of respective segment 220. Therefore, values of a respective fluorescence peak 304 and a respective peak wavelength 306 associated with respective segment 220 may be subjected to inter-segment interferences from adjacent segments of respective segment 220. In an exemplary embodiment, spatial and digital filtering may be utilized to suppress an impact of inter-segment interferences. In an exemplary embodiment, a signal-to-noise ratio (SNR) of the plurality of fluorescence spectra may be increased by utilizing time-frequency transforms and wavelet transform de-noising.

For further detail with respect to step 108, in an exemplary embodiment, the plurality of fluorescence peaks may be detected by detecting respective fluorescence peak 304 of the plurality of fluorescence peaks in each of the plurality of fluorescence spectra. In an exemplary embodiment, the plurality of peak wavelengths may be detected by detecting respective peak wavelength 306 of the plurality of peak wavelengths in each of the plurality of fluorescence spectra. In an exemplary embodiment, respective peak wavelength 306 may be associated with respective fluorescence peak 304. In an exemplary embodiment, the plurality of fluorescence peaks and the plurality of peak wavelengths may be detected utilizing processor 208.

Figure 4:
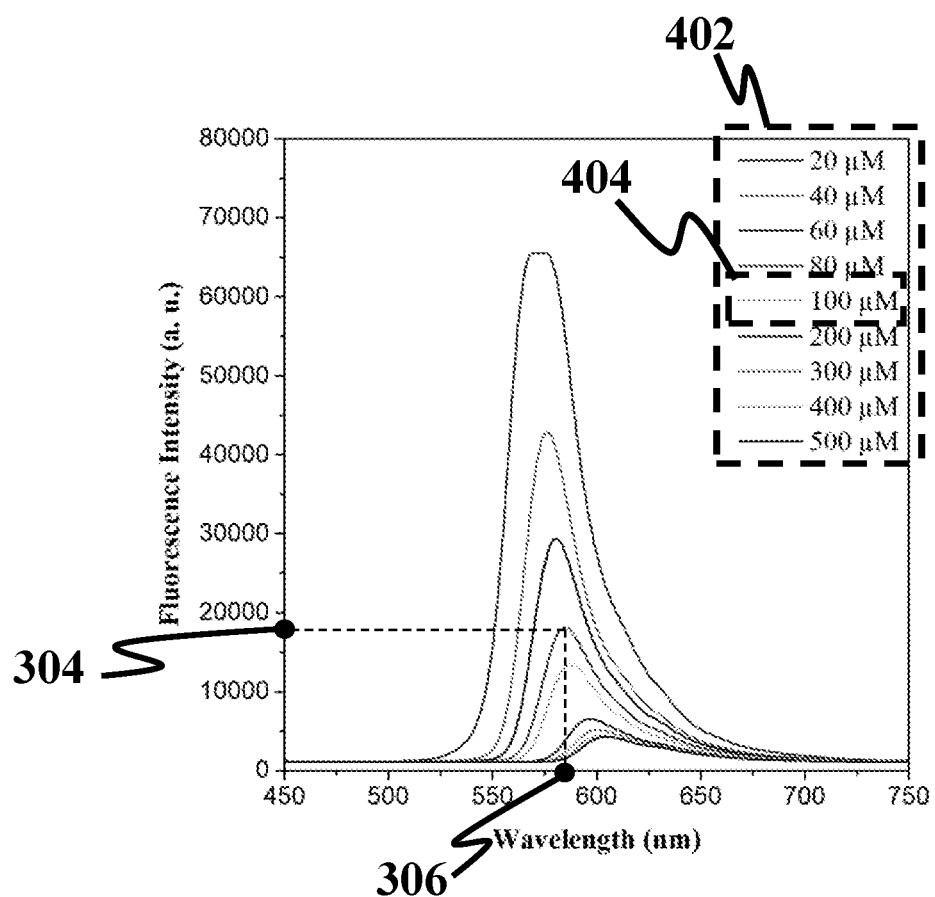
FIG. 4 shows a database including variations of fluorescence intensity with wavelength for different concentrations of a fluorophore, consistent with one or more exemplary embodiments of the present disclosure.

For further detail with respect to step 110, FIG. 4 shows an exemplary database including variations of fluorescence intensity with wavelength for different concentrations of a fluorophore, consistent with one or more exemplary embodiments of the present disclosure. In an exemplary embodiment, a database 400 may be associated with the laser wavelength and may include variations of fluorescence intensity with wavelength for different concentrations of the fluorophore. In an exemplary embodiment, each of the plurality of fluorophore concentrations may be associated with respective peak wavelength 306 of the plurality of peak wavelengths. In an exemplary embodiment, the plurality of fluorophore concentrations may be extracted from dtatbase 400 utilizing processor 208.

Referring again to FIGS. 2B-4, when stimulated by laser beam 214, each segment of plurality of segments 212 may emit respective fluorescence emission 218 with respective peak wavelength 306. A difference between the laser wavelength and respective peak wavelength 306 may be referred to as a spectral shift. Therefore, in an exemplary embodiment, respective peak wavelength 306 may correspond to a respective spectral shift for respective segment 220.

For a specific concentration, an exemplary fluorophore may emit a fluorescence emission with a specific fluorescence spectrum, i.e., a specific fluorescence peak and a specific peak wavelength. Generally, increasing fluorophore concentration may lead to a lower fluorescence peak and a higher peak wavelength. In an exemplary embodiment, database 400 may include a one-to-one relationship between a fluorescence peak and concentration of the fluorophore. Moreover, in an exemplary embodiment, database 400 may include another one-to-one relationship between a peak wavelength and concentration of the fluorophore. In an exemplary embodiment, respective peak wavelength 306 for each segment of plurality of segments 212 may correspond to a unique spectral shift for each segment of plurality of segments 212. Therefore, a one-to-one relationship between a peak wavelength and concentration may be obtained for an exemplary fluorophore.

In an exemplary embodiment, a relationship between the peak wavelength and a fluorophore concentration may depend on an angle between laser beam 214 and respective fluorescence emission 218. Therefore, in an exemplary embodiment, database 400 may be generated for a predefined angle between laser beam 214 and respective fluorescence emission 218. An exemplary predefined angle may be set to zero to facilitate emitting laser beam 214 and capturing respective fluorescence emission 218 utilizing optical microscope 222. Hence, in an exemplary embodiment, respective fluorescence emission 218 may be captured in parallel to laser beam 214. For this purpose, in an exemplary embodiment, main axis 242 of tip 240 may be configured to be in the direction of laser beam 214.

Figure 5A:
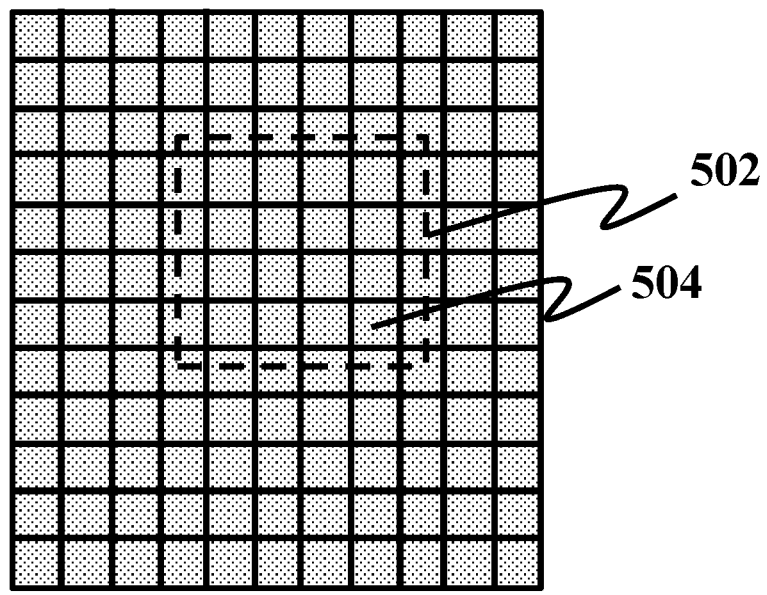
FIG. 5A shows a concentration image, consistent with one or more exemplary embodiments of the present disclosure.

For further detail with respect to step 112, FIG. 5A shows a concentration image, consistent with one or more exemplary embodiments of the present disclosure. In an exemplary embodiment, a concentrationimge 500A may include a first plurality of pixels 502 and may be generated by assigning a respective intensity level to each of first plurality of pixels 502 based on a respective fluorophore concentration 404 of the plurality of fluorophore concentrations 402. In an exemplary embodiment, respective fluorophore concentration 404 may be associated with respective segment 220 of plurality of segments 212. In an exemplary embodiment, concentration image 500A may be generated utilizing processor 208.

In an exemplary embodiment, spectrometer 204 may include a spectroscopy resolution. An exemplary spectroscopy resolution may refer to a minimum difference between two wavelengths that may be distinguishable by spectrometer 204. An exemplary spectroscopy resolution may determine a precision of determining a spectral shift. Since there may be a one-to-one relationship between a spectral shift and concentration, an exemplary spectroscopy resolution may influence a precision of determining concentration. Therefore, in an exemplary embodiment, a spectrometer with a higher spectroscopy resolution may facilitate providing a better quality for concentration image 500A.

Figure 5B:
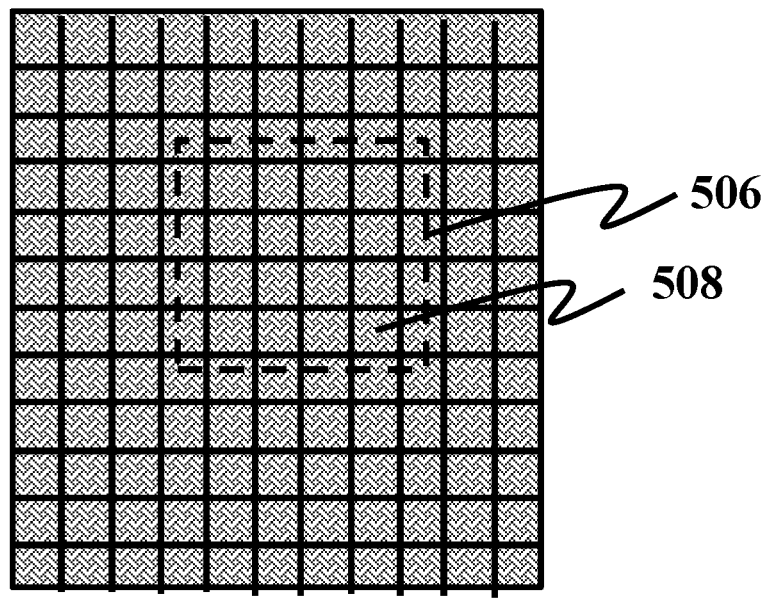
FIG. 5B shows a fluorescence image, consistent with one or more exemplary embodiments of the present disclosure.

For further detail with respect to step 114, FIG. 5B shows a fluorescence image, consistent with one or more exemplary embodiments of the present disclosure. In an exemplary embodiment, a fluorescence image 500B may include a second plurality of pixels 506. In an exemplary embodiment, fluorescence image 500B may be generated by assigning a respective intensity level to each of the second plurality of pixels based on respective fluorescence peak 304. In an exemplary embodiment, respective fluorescence peak 304 may be associated with respective segment 220 of plurality of segments 212. In an exemplary embodiment, a respective pixel 508 of second plurality of pixels 506 may be associated with respective segment 220.

In an exemplary embodiment, obtaining respective fluorescence peak 304 for each segment of plurality of segments 212 may provide a distribution of concentration of the fluorophore over sample 210. On the other hand, in an exemplary embodiment, obtaining spectral shift for each segment of plurality of segments 212 may provide another distribution of concentration of the fluorophore over sample 210. In an exemplary embodiment, due to several phenomena that may impact respective fluorescence peak 304 for each segment of plurality of segments 212, a distribution of concentration obtained from the plurality of fluorescence peaks may differ from a distribution of concentration obtained from the plurality of peak wavelengths.

In an exemplary embodiment, a field of view of second eyepiece 237 may impact sizes of plurality of segments 212. Larger field of view of second eyepiece 237 may result in larger sizes of plurality of segments 212. In an exemplary embodiment, the size of plurality of segments 212 may determine sizes of first plurality of pixels 502 and second plurality of pixels 506. For example, larger sizes of plurality of segments 212 may result in larger sizes of first plurality of pixels 502 and second plurality of pixels 506. Moreover, in an exemplary embodiment, a precision of translation stage 228 may impact sizes of plurality of segments 212. In an exemplary embodiment, a higher precision of translation stage 228 may result in smaller sizes of plurality of segments 212. In an exemplary embodiment, lower precision of translation stage 228 may result in larger sizes of plurality of segments 212.

Referring again to FIGS. 2A-2B, in an exemplary embodiment, optical microscope 222 may comprise a confocal laser scanning microscope. A confocal laser scanning microscope may refer to a microscope with an ability to focus a laser beam at various focal points of various depths. In an exemplary embodiment, optical microscope 222 may place focal point 230 at various depths of sample 210. In this case, a cross-section 234 may be associated with focal point 230 at each depth. In an exemplary embodiment, utilizing method 100 may provide 2D images (i.e., concentration image 500A in FIG. 5A and fluorescence image 500B in FIG. 5B) associated with cross-section 234. By repeating method 100 for different cross-sections of sample 210, several 2D images may be obtained. Therefore, a 3D concentration image and a 3D fluorescence image may be obtained by stacking 2D images associated with different depths.

In an exemplary embodiment, memory 206 may have processor-readable instructions stored therein. In an exemplary embodiment, processor 208 may be configured to access memory 206 and execute the processor-readable instructions. In an exemplary embodiment, the processor-readable instructions may configure processor 208 to perform steps 108-114 of method 100.

Figure 6:
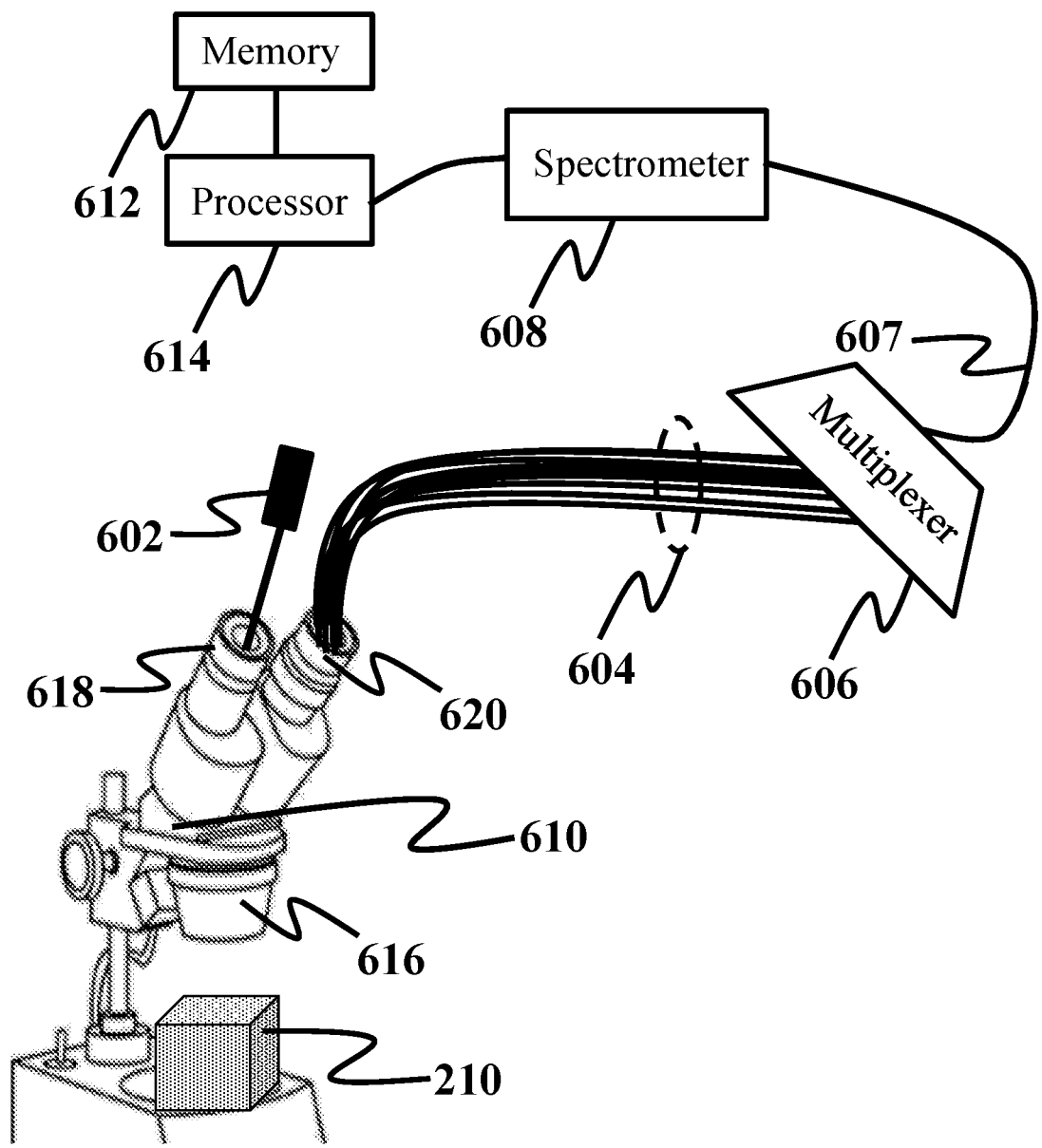
FIG. 6 shows a schematic of a system for optical imaging with a plurality of optical fibers, consistent with one or more exemplary embodiments of the present disclosure.

FIG. 6 shows a schematic of a system for optical imaging with a plurality of optical fibers, consistent with one or more exemplary embodiments of the present disclosure. In an exemplary embodiment, system 600 may include a laser 602, a plurality of optical fibers 604, a fiber optic multiplexer 606, an optical fiber 607, a spectrometer 608, an optical microscope 610, a memory 612, and a processor 614. In an exemplary embodiment, laser 602 may be similar to laser 202. In an exemplary embodiment, each of plurality of optical fibers 604 may be configured to capture a respective fluorescence emission of a plurality of fluorescence emissions. In an exemplary embodiment, the respective fluorescence emission may be similar to respective fluorescence emission 218. In an exemplary embodiment, fiber optic multiplexer 606 may be configured to receive the plurality of fluorescence emissions. In an exemplary embodiment, fiber optic multiplexer 606 may further be configured to generate a multiplexed fluorescence emission. In an exemplary embodiment, the multiplexed fluorescence emission may include the plurality of fluorescence emissions. In an exemplary embodiment, fiber optic multiplexer 606 may be configured to send the multiplexed fluorescence emission over optical fiber 607. In an exemplary embodiment, spectrometer 608 may be configured to receive the multiplexed fluorescence emission from optical fiber 607. In an exemplary embodiment, spectrometer 608 may also be configured to extract a plurality of fluorescence spectra from the plurality of fluorescence emissions. In an exemplary embodiment, the plurality of fluorescence spectra may be extracted by extracting a respective fluorescence spectrum of the plurality of fluorescence spectra from each of the plurality of fluorescence emissions. In an exemplary embodiment, optical microscope 610 may include an objective lens 616, a first eyepiece 618 and a second eyepiece 620. In an exemplary embodiment, objective lens 616 may be similar to objective lens 224. In an exemplary embodiment, first eyepiece 618 may be configured to focus a laser beam on sample 210. In an exemplary embodiment, second eyepiece 620 may be configured to send the plurality of fluorescence emissions to plurality of optical fibers 604. In an exemplary embodiment, the plurality of fluorescence emissions may be sent by sending the respective fluorescence emission to the respective optical fiber. In other words, each exemplary fluorescence emission may be sent to a separate optical fiber of plurality of optical fibers 604. In exemplary embodiment, memory 612 may be similar to memory 206. In an exemplary embodiment, processor 614 may be similar to processor 208. In an exemplary embodiment, plurality of optical fibers 604 may simultaneously capture the plurality of fluorescence emissions. Therefore, in an exemplary embodiment, system 600 may not require a translation stage since every optical fiber of plurality of optical fibers 604 may be placed on a separate respective segment of sample 210. Moreover, in case of in vivo imaging, system 600 may be utilized for imaging of a sample including a biological tissue. In this case, plurality of optical fibers 604 may simultaneously capture the plurality of fluorescence emissions without needing a translation stage. In an exemplary embodiment, each of the plurality of optical fibers may include a tip (not illustrated in FIG. 6) similar to tip 240 in FIG. 2B.

Figure 7:
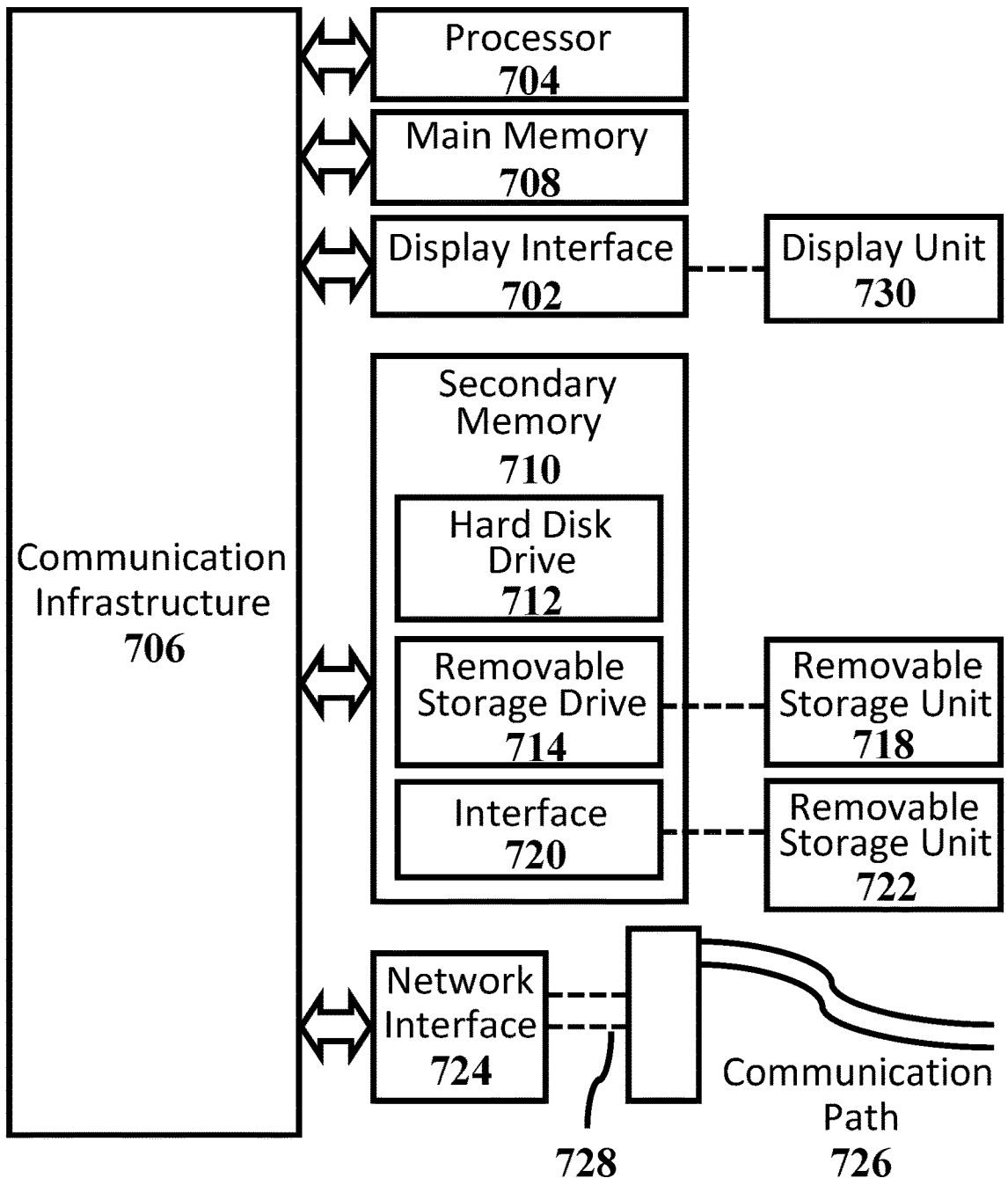
FIG. 7 shows a high-level functional block diagram of a computer system, consistent with one or more exemplary embodiments of the present disclosure.

FIG. 7 shows an example computer system 700 in which an embodiment of the present invention, or portions thereof, may be implemented as computer-readable code, consistent with exemplary embodiments of the present disclosure. For example, method 100 may be implemented in computer system 700 using hardware, software, firmware, tangible computer readable media having instructions stored thereon, or a combination thereof and may be implemented in one or more computer systems or other processing systems. Hardware, software, or any combination of such may embody any of the modules and components in FIGS. 1A-6.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multiprocessor machines. In addition, in some embodiments the order of operations may be rearranged without departing from the spirit of the disclosed subject matter.

Processor device 704 may be a special purpose or a general-purpose processor device. As will be appreciated by persons skilled in the relevant art, processor device 704 may also be a single processor in a multi-core/multiprocessor system, such system operating alone, or in a cluster of computing devices operating in a cluster or server farm. Processor device 704 may be connected to a communication infrastructure 706, for example, a bus, message queue, network, or multi-core message-passing scheme.

In an exemplary embodiment, computer system 700 may include a display interface 502, for example a video connector, to transfer data to a display unit 730, for example, a monitor. Computer system 700 may also include a main memory 708, for example, random access memory (RAM), and may also include a secondary memory 710. Secondary memory 710 may include, for example, a hard disk drive 712, and a removable storage drive 714. Removable storage drive 714 may include a floppy disk drive, a magnetic tape drive, an optical disk drive, a flash memory, or the like. Removable storage drive 714 may read from and/or write to a removable storage unit 718 in a well-known manner. Removable storage unit 718 may include a floppy disk, a magnetic tape, an optical disk, etc., which may be read by and written to by removable storage drive 714. As will be appreciated by persons skilled in the relevant art, removable storage unit 718 may include a computer usable storage medium having stored therein computer software and/or data.

In alternative implementations, secondary memory 710 may include other similar means for allowing computer programs or other instructions to be loaded into computer system 700. Such means may include, for example, a removable storage unit 722 and an interface 720. Examples of such means may include a program cartridge and cartridge interface (such as that found in video game devices), a removable memory chip (such as an EPROM, or PROM) and associated socket, and other removable storage units 722 and interfaces 520 which allow software and data to be transferred from removable storage unit 722 to computer system 700.

Computer system 700 may also include a communications interface 724. Communications interface 724 allows software and data to be transferred between computer system 700 and external devices. Communications interface 724 may include a modem, a network interface (such as an Ethernet card), a communications port, a PCMCIA slot and card, or the like. Software and data transferred via communications interface 724 may be in the form of signals, which may be electronic, electromagnetic, optical, or other signals capable of being received by communications interface 724. These signals may be provided to communications interface 724 via a communications path 726. Communications path 726 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 718, removable storage unit 722, and a hard disk installed in hard disk drive 712. Computer program medium and computer usable medium may also refer to memories, such as main memory 508 and secondary memory 710, which may be memory semiconductors (e.g. DRAMs, etc.).

Computer programs (also called computer control logic) are stored in main memory 708 and/or secondary memory 710. Computer programs may also be received via communications interface 724. Such computer programs, when executed, enable computer system 700 to implement different embodiments of the present disclosure as discussed herein. In particular, the computer programs, when executed, enable processor device 704 to implement the processes of the present disclosure, such as the operations in method 100 illustrated by flowchart 100 of FIG. 1A discussed above. Accordingly, such computer programs represent controllers of computer system 700. Where an exemplary embodiment of method 100 is implemented using software, the software may be stored in a computer program product and loaded into computer system 700 using removable storage drive 714, interface 720, and hard disk drive 712, or communications interface 724.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nano-technological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

Example 1

In this example, a performance of a method (analogous to method 100) for optical imaging based on spectral shift assessment is demonstrated. Different steps of the method are implemented using a system for optical imaging based on spectral shift assessment (analogous to system 200). A tip size of an exemplary optical fiber (analogous to optical fiber 236) is about 500 μm and a field of view of a second eyepiece (analogous to second eyepiece 237) is about 50 μm.

Figure 8A:
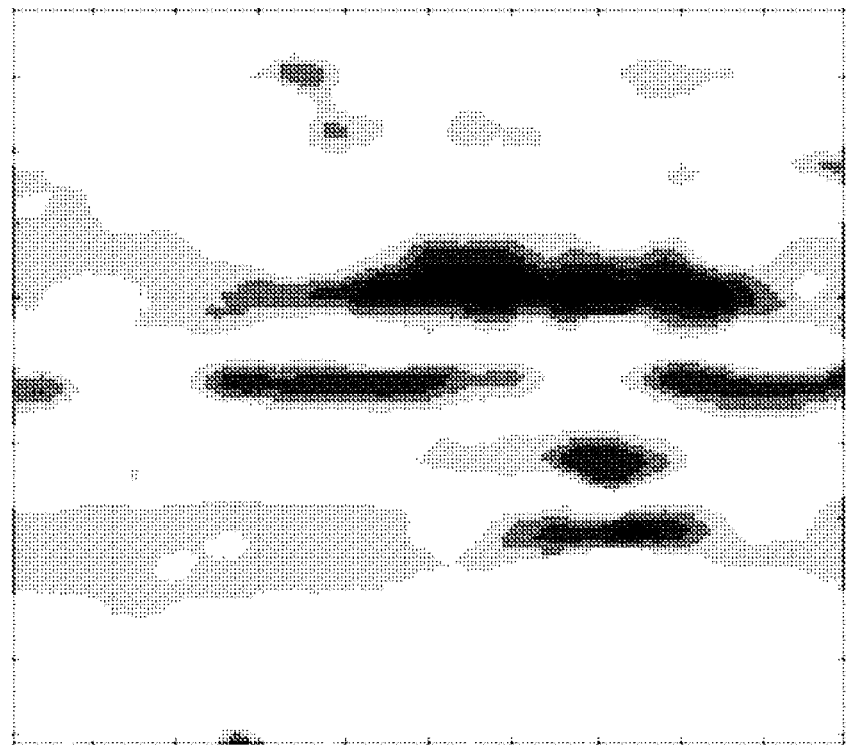
FIG. 8A shows a concentration image of a sample including an apple tissue, consistent with one or more exemplary embodiments of the present disclosure.
Figure 8B:
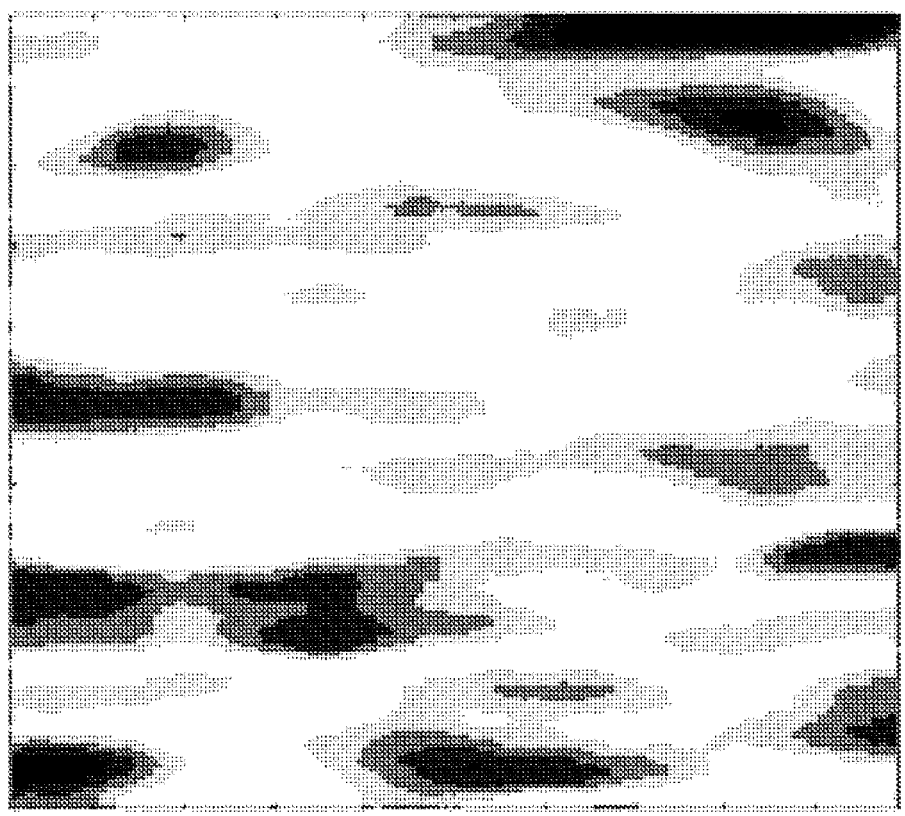
FIG. 8B shows a fluorescence image of a sample including an apple tissue, consistent with one or more exemplary embodiments of the present disclosure.

A size of each segment of a plurality of segments (analogous to plurality of segments 212) is about 3 μm. The system includes a spectrometer (analogous to spectrometer 204) with a 2048 pixel charge-coupled device (CCD) array and with about 4 nm spectrum resolution. The system also includes a micrometer translation stage (analogous to translation stage 228) which sweeps a sample (analogous to sample 210) with about 6 μm step size. Objects of interest include apple and onion tissues with a dimension about 1 cm×1 cm and a thickness of about 2 to 3 mm. The sample is generated by mixing an apple tissue with a fluorophore. The fluorophore includes Rhodamine-B solved in ethanol with 40 μM concentration. A laser (analogous to laser 202) is utilized to stimulate the sample which is of type SHG CW Nd:YAG with 532 nm laser wavelength and 10 mW power. FIG. 8A shows a concentration image of a sample including an apple tissue, consistent with one or more embodiments of the present disclosure. FIG. 8B shows a fluorescence image of a sample including an apple tissue, consistent with one or more embodiments of the present disclosure. As FIGS. 8A and 8B show, the concentration image and the fluorescence image differ for a single sample. Moreover, the concentration image provides a more detailed information about the sample.

Example 2

Figure 9A:
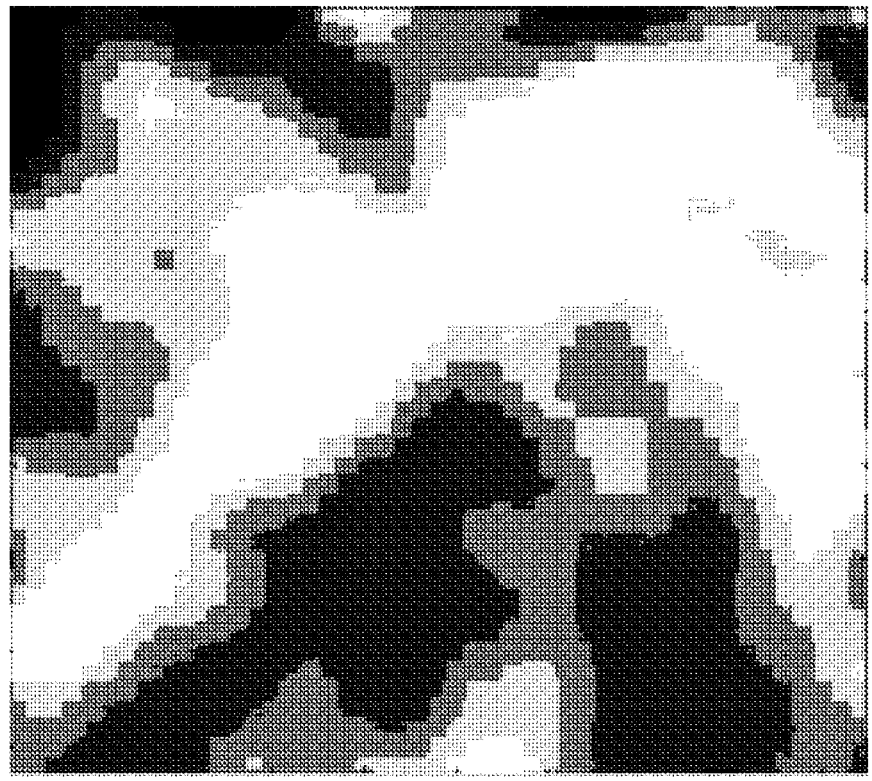
FIG. 9A shows a concentration image of a sample including an onion tissue, consistent with one or more exemplary embodiments of the present disclosure.
Figure 9B:
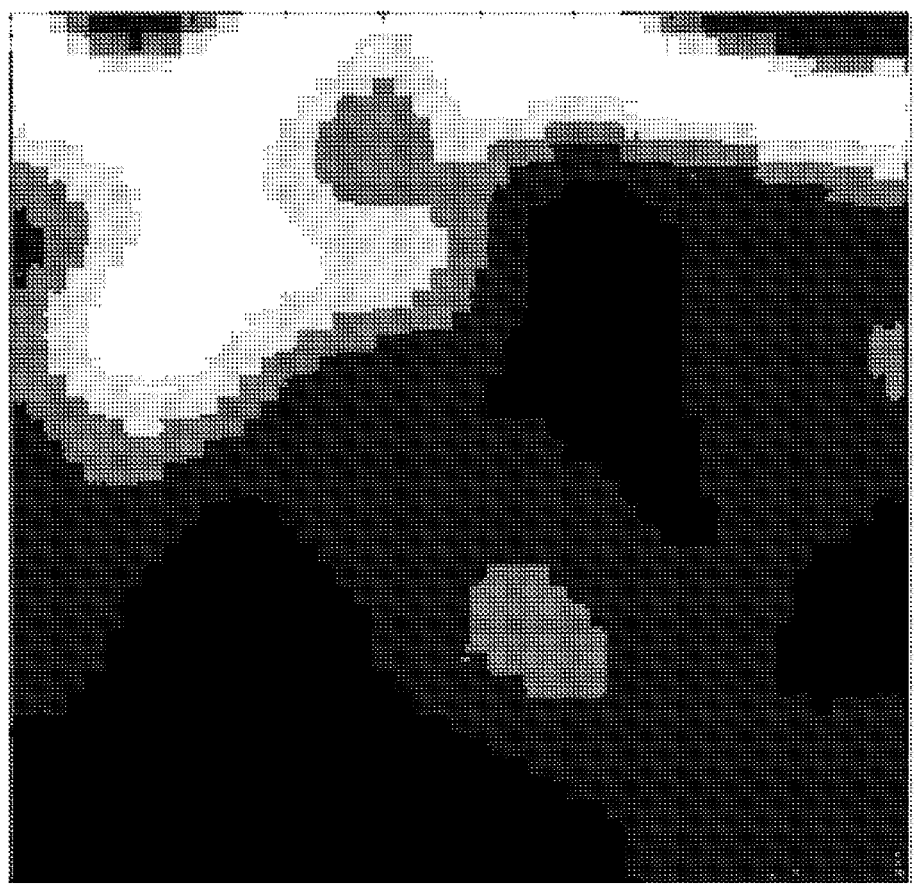
FIG. 9B shows a fluorescence image of a sample including an onion tissue, consistent with one or more exemplary embodiments of the present disclosure.

In this example, a system similar to the system of EXAMPLE 1 is considered except for a generated sample and a utilized laser. An exemplary sample is generated by mixing an onion tissue with a fluorophore, consistent with step 102 of method 100. The fluorophore includes fluorescein solved in deionized water with a 5 μM concentration. A laser (analogous to laser 202) is utilized to stimulate the sample which is of a type GaN diode with a 405 nm laser wavelength and a 10 mW power. FIG. 9A shows a concentration image of a sample including an onion tissue, consistent with one or more embodiments of the present disclosure. FIG. 8B shows a fluorescence image of a sample including an onion tissue, consistent with one or more embodiments of the present disclosure. As FIGS. 9A and 9B show, the concentration image and the fluorescence image differ for a single sample. Moreover, the concentration image provides a more detailed information about the sample.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for optical imaging based on spectral shift assessment, the method comprising:

generating a sample by mixing an object with a fluorophore, the sample comprising a plurality of segments;

stimulating the sample by emitting a laser beam on each of the plurality of segments, the laser beam comprising a laser wavelength;

extracting, utilizing a spectrometer, a plurality of fluorescence spectra from a plurality of fluorescence emissions emitted from the sample by extracting each of the plurality of fluorescence spectra from a respective fluorescence emission of the plurality of fluorescence emissions, the respective fluorescence emission emitted from a respective segment of the plurality of segments;

detecting, utilizing one or more processors, a plurality of fluorescence peaks and a plurality of peak wavelengths in the plurality of fluorescence spectra by detecting a respective fluorescence peak of the plurality of fluorescence peaks and a respective peak wavelength of the plurality of peak wavelengths in each of the plurality of fluorescence spectra, the respective peak wavelength associated with the respective fluorescence peak;

extracting, utilizing the one or more processors, a plurality of fluorophore concentrations from a database associated with the laser wavelength, the database comprising variations of fluorescence intensity with wavelength for different concentrations of the fluorophore, each of the plurality of fluorophore concentrations associated with a respective peak wavelength of the plurality of peak wavelengths;

generating, utilizing the one or more processors, a concentration image comprising a first plurality of pixels by assigning a respective intensity level to each of the first plurality of pixels based on a respective fluorophore concentration of the plurality of fluorophore concentrations, the respective fluorophore concentration associated with a respective segment of the plurality of segments.

2. The method of claim 1, further comprising generating a fluorescence image comprising a second plurality of pixels by assigning a respective intensity level to each of the second plurality of pixels based on a respective fluorescence peak associated with a respective segment of the plurality of segments.

3. The method of claim 1, wherein stimulating the sample by emitting the laser beam comprises:
placing the sample under an objective lens of an optical microscope;
focusing the laser beam on each of the plurality of segments by passing the laser beam through a first eyepiece of the optical microscope.

4. The method of claim 3, wherein focusing the laser beam on each of the plurality of segments comprises positioning a focal point of the laser beam at a respective center of each of the plurality of segments by moving the respective center to a location of the focal point utilizing a translation stage.

5. The method of claim 3, wherein extracting each of the plurality of fluorescence spectra from the respective fluorescence emission comprises:
capturing the respective fluorescence emission by an optical fiber; and
sending the respective fluorescence emission to the spectrometer via the optical fiber.

6. The method of claim 5, wherein capturing the respective fluorescence emission comprises capturing the respective fluorescence emission through an emission path comprising the objective lens and a second eyepiece of the optical microscope.

7. The method of claim 5, wherein capturing the respective fluorescence emission by the optical fiber comprises positioning a main axis of a tip of the optical fiber in a direction of the laser beam.

8. The method of claim 1, wherein mixing the object with the fluorophore comprises mixing each of the plurality of segments with the fluorophore, each of the plurality of segments comprising a biological material.

9. The method of claim 8, wherein mixing the object with the fluorophore comprises injecting a biocompatible fluorophore into a biological tissue.

10. The method of claim 8, wherein mixing the biological tissue with the fluorophore comprises mixing the biological tissue with one of Rhodamine 6G (RD6G), coumarin, or fluorescein.

11. A system for optical imaging based on spectral shift assessment, the system comprising:
a laser configured to stimulate a sample comprising a plurality of segments by emitting a laser beam comprising a laser wavelength on each of the plurality of segments, each segment of the plurality of segments comprising a respective mixture of a fluorophore and a biological material;
a plurality of optical fibers, each of the plurality of optical fibers configured to capture a respective fluorescence emission of a plurality of fluorescence emissions, the respective fluorescence emission emitted from a respective segment of the plurality of segments;
a fiber optic multiplexer configured to:
receive the plurality of fluorescence emissions from the plurality of optical fibers; and
generate a multiplexed fluorescence emission from the plurality of fluorescence emissions, the multiplexed fluorescence emission comprising the plurality of fluorescence emissions;
a spectrometer comprising an input optical fiber configured to receive the multiplexed fluorescence emission from the fiber optic multiplexer, the spectrometer configured to extract a plurality of fluorescence spectra from the plurality of fluorescence emissions by extracting a respective fluorescence spectrum of the plurality of fluorescence spectra from the multiplexed fluorescence emission;
an optical microscope comprising:
an objective lens configured to be placed above the sample;
a first eyepiece configured to focus the laser beam on the sample; and
a second eyepiece configured to:
receive the plurality of fluorescence emissions through the objective lens; and
send the plurality of fluorescence emissions to the plurality of optical fibers by sending the respective fluorescence emission to the respective optical fiber;
a memory having processor-readable instructions stored therein; and
one or more processors configured to access the memory and execute the processor-readable instructions, which, when executed by the processor configures the one or more processors to perform a method, the method comprising:
detecting a plurality of fluorescence peaks and a plurality of peak wavelengths in the plurality of fluorescence spectra by detecting a respective fluorescence peak of the plurality of fluorescence peaks and a respective peak wavelength of the plurality of peak wavelengths in each of the plurality of fluorescence spectra, the respective peak wavelength associated with the respective fluorescence peak;

extracting a plurality of fluorophore concentrations from a database associated with the laser wavelength, the database comprising variations of fluorescence intensity with wavelength for different concentrations of the fluorophore, each of the plurality of fluorophore concentrations associated with a respective peak wavelength of the plurality of peak wavelengths;

generating a concentration image comprising a first plurality of pixels by assigning a respective intensity level to each of the first plurality of pixels based on a respective fluorophore concentration of the plurality of fluorophore concentrations, the respective fluorophore concentration associated with a respective segment of the plurality of segments; and generating a fluorescence image comprising a second plurality of pixels by assigning a respective intensity level to each of the second plurality of pixels based on a respective fluorescence peak associated with a respective segment of the plurality of segments.

12. The system of claim 11, wherein each of the plurality of optical fibers comprises a tip comprising a main axis configured to be positioned in a direction of the laser beam.

13. A system for optical imaging based on spectral shift assessment, the system comprising:
a laser configured to stimulate a sample comprising a plurality of segments by emitting a laser beam comprising a laser wavelength on each of the plurality of segments, each segment of the plurality of segments comprising a respective mixture of a fluorophore and a biological material;
a spectrometer configured to extract a plurality of fluorescence spectra from a plurality of fluorescence emissions emitted from the sample by extracting each of the plurality of fluorescence spectra from a respective fluorescence emission of the plurality of fluorescence emissions, the respective fluorescence emission emitted from a respective segment of the plurality of segments;
a memory having processor-readable instructions stored therein; and
one or more processors configured to access the memory and execute the processor-readable instructions, which, when executed by the processor configures the one or more processors to perform a method, the method comprising:
detecting a plurality of fluorescence peaks and a plurality of peak wavelengths in the plurality of fluorescence spectra by detecting a respective fluorescence peak of the plurality of fluorescence peaks and a respective peak wavelength of the plurality of peak wavelengths in each of the plurality of fluorescence spectra, the respective peak wavelength associated with the respective fluorescence peak;

extracting a plurality of fluorophore concentrations from a database associated with the laser wavelength, the database comprising variations of fluorescence intensity with wavelength for different concentrations of the fluorophore, each of the plurality of fluorophore concentrations associated with a respective peak wavelength of the plurality of peak wavelengths; and generating a concentration image comprising a first plurality of pixels by assigning a respective intensity level to each of the first plurality of pixels based on a respective fluorophore concentration of the plurality of fluorophore concentrations, the respective fluorophore concentration associated with a respective segment of the plurality of segments.

14. The system of claim 13, wherein the method further generating a fluorescence image comprising a second plurality of pixels by assigning a respective intensity level to each of the second plurality of pixels based on a respective fluorescence peak associated with a respective segment of the plurality of segments.

15. The system of claim 13, further comprising an optical fiber configured to:
capture the respective fluorescence emission; and
send the respective fluorescence emission to the spectrometer.

16. The system of claim 15, further comprising an optical microscope comprising:
an objective lens configured to be placed above the sample;
a first eyepiece configured to focus the laser beam on each of the plurality of segments; and
a second eyepiece configured to:
receive the respective fluorescence emission through the objective lens; and
send the respective fluorescence emission to the optical fiber.

17. The system of claim 16, further comprising a translation stage configured to position a focal point of the laser beam at a respective center of each of the plurality of segments by moving the respective center to a location of the focal point.

18. The system of claim 16, wherein the optical microscope comprises a confocal laser scanning microscope.

19. The system of claim 15, wherein the optical fiber comprises a tip comprising a main axis configured to be positioned in a direction of the laser beam.

20. The system of claim 13, further comprising a needle configured to generate the sample by injecting the fluorophore into the biological material, the fluorophore comprising a biocompatible fluorophore.

* * * * *